United States Patent
Coates et al.

(10) Patent No.: US 7,560,523 B2
(45) Date of Patent: Jul. 14, 2009

(54) PRODUCTION OF ISOTACTIC AND REGIORANDOM POLYPROPYLENE BASED POLYMER AND BLOCK COPOLYMERS

(75) Inventors: Geoffrey W. Coates, Ithaca, NY (US); Anna Cherian, Ithaca, NY (US); Jeffrey M. Rose, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/508,333

(22) Filed: Aug. 23, 2006

(65) Prior Publication Data

US 2007/0123668 A1    May 31, 2007

Related U.S. Application Data

(60) Provisional application No. 60/710,876, filed on Aug. 25, 2005.

(51) Int. Cl.
*C08F 210/06* (2006.01)
*C08F 10/06* (2006.01)

(52) U.S. Cl. .................. 526/348; 526/351; 526/352; 528/396

(58) Field of Classification Search .......... 526/348, 526/352, 351; 528/396
See application file for complete search history.

(56) References Cited

U.S. PATENT DOCUMENTS

| | | | | |
|---|---|---|---|---|
| 6,469,100 | B2 * | 10/2002 | Suzuki et al. | 525/88 |
| 6,635,733 | B2 * | 10/2003 | Yahata et al. | 526/348 |
| 6,737,487 | B2 | 5/2004 | Meverden | |
| 6,916,886 | B2 * | 7/2005 | Morioka et al. | 525/323 |
| 6,995,279 | B2 * | 2/2006 | Ushioda et al. | 556/11 |
| 7,081,493 | B2 * | 7/2006 | Kawai et al. | 524/505 |
| 7,105,604 | B2 * | 9/2006 | Shimizu et al. | 525/191 |
| 2003/0187121 | A1 * | 10/2003 | Kawai et al. | 524/451 |
| 2004/0127731 | A1 * | 7/2004 | Ushioda et al. | 556/53 |
| 2005/0131160 | A1 * | 6/2005 | Shimizu et al. | 525/242 |

OTHER PUBLICATIONS

Cherian, A.E., et al., "A $C_2$-Symmetric, Living α-Diimine Ni(II) Catalyst: Regioblock Copolymers from Propylene", J. Am. Chem. Soc. 2005, 127, 13770-13771, and Supporting Information.
Cherian, A.E., et al., "Acid-Catalyzed ortho-Alkylation of Anilines with Styrenes: An Improved Route to Chiral Anilines with Bulky Substituents", Organic Letters, 2005, vol. 7, No. 23, 5135-5137, Published on Web Oct. 13, 2005, and Supporting Information.

* cited by examiner

*Primary Examiner*—David Wu
*Assistant Examiner*—Rip A. Lee
(74) *Attorney, Agent, or Firm*—Bacon & Thomas, PLLC

(57) ABSTRACT

One step ortho-alkylation of anilines with styrenes to give chiral anilines is obtained using a strong acid catalyst, e.g. $CF_3SO_3H$. Condensation of the product to give ligand and metallation gives complex which catalyzes polymerization of propylene to give isotactic propylene or regiorandom propylene of low PDI or blocks thereof, depending on polymerization temperature.

4 Claims, No Drawings

PRODUCTION OF ISOTACTIC AND REGIORANDOM POLYPROPYLENE BASED POLYMER AND BLOCK COPOLYMERS

CROSS-REFERENCE TO RELATED APPLICATIONS

This application claims the benefit of U.S. Provisional Patent Application No. 60/710,876, filed Aug. 25, 2005, the whole of which is incorporated herein by reference.

This invention was made at least in part with U.S. Government Support under U.S. Army Research Laboratory and U.S. Army Research Office Grant Number DAAD 19-02-1-0275 Macromolecular Architecture for Performance (MAP) MURI and making use of the Cornell Center for Materials Research Shared Experimental Facilities supported through the NSF MRSEC program (DMR-0079992). The U.S. Government has certain rights in the invention.

TECHNICAL FIELD

This invention is directed to the method of synthesizing anilines, complex containing transition metal useful to catalyze preparation of isotactic and/or regiorandom polypropylene and block polymer containing one or more blocks of at least one of these, compound useful to prepare the complex, regiorandom polypropylene and plural block copolymer containing at least one block of regiorandom polypropylene and/or polyethylene with attached methyl groups.

BACKGROUND OF THE INVENTION

Catalysts that are more functional group tolerant for polymerizing functional alkenes and show living behavior, generally produce amorphous atactic polymers.

We conceived that anilines with ortho-substituents containing stereogenic centers would be universal building blocks for a wide array of stereoselective catalysts. Our initial effort was directed to synthesis of bulky chiral substituents for incorporation into an α-diimine Ni(II) catalyst for the isospecific polymerization of trans-2-butene; this work is described in Cherian, A. E., Chem. Commum. 20, 3565-2567 (2003). This work relied on the zeolite-catalyzed reaction of phenylacetylene and p-toluidine as described in Arienti, A., et al., Tetrahedron 53, 3795-3804 (1997), followed by subsequent hydrogenation of the resulting 2,6-bis(1-phenyl vinyl) anilines catalyzed by Pd/C. However, the scope of anilines that could be synthesized by this method was limited and the synthesis required two steps.

SUMMARY OF THE INVENTION

It has been discovered herein that reaction of para-substituted anilines with styrene derivatives when catalyzed by strong acid results in highly chemoselective ortho-alkylation of the anilines.

It has also been discovered herein that $C_2$-symmetric complexes formed from these anilines in the presence of methylaluminoxane or other cocatalysts, e.g. $Et_2AlCl$, catalyze formation of either isotactic polypropylene or regiorandom polypropylene depending on the polymerization temperature.

As used herein the term $C_2$-symmetric means obtaining an identical molecule on 180° rotation.

As used herein, the term regiorandom polypropylene means having the structure

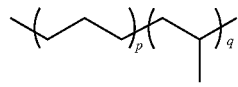

where the percentage of p units is at least 1%, typically 15% or greater, but not higher than 99%.

As used herein the term 3,1 insertion in respect to polymerization of propylene means formation of

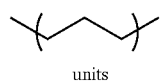

units

Regiorandom polypropylene is similar in structure and properties to commercially made poly(ethylene-co-propylene) (EPR) which is a rubbery material with a low $T_g$ and is useful in many commercial applications. The regiorandom polypropylene herein offers advantages over EPR, including controlled molecular weight and molecular weight distribution, and no ethylene runs (ethylene runs in commercial EPR cause small regions of crystallinity in the otherwise amorphous polymer). As a mid-block, the regiorandom polypropylene herein, is an exceptional material because it has such low $T_g$, e.g., 0° C. to −60° C., and is very soft and pliable.

One embodiment herein, denoted the first embodiment, is directed to a method of synthesizing a chiral aniline having the structure

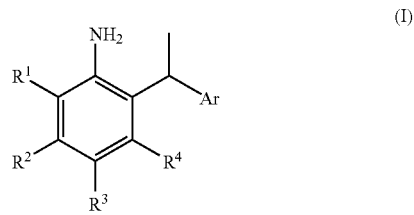

where $R^1$, $R^2$, $R^3$ and $R^4$ may be the same or different, and are each a hydrogen atom, a halogen atom, a fluorocarbon group, a heterocyclic compound residue, an oxygen-containing group, a nitrogen-containing group, a boron-containing group, a sulfur-containing group, a phosphorus-containing group, a carbon containing group, e.g., containing from 1 to 20 carbon atoms, a silicon-containing group, and two or more of them may be bonded to each other to form a ring or rings, and Ar is selected from the group consisting of aromatic hydrocarbon or heterocycle optionally substituted with one or more hydrogen atoms, halogen atoms, fluorocarbon groups, heterocyclic compound residues, oxygen-containing groups, nitrogen-containing groups, boron-containing groups, sulfur-containing groups, phosphorus-containing groups, carbon-containing groups (such as hydrocarbons containing 1 to 20 carbon atoms), or a silicon-containing groups, and two or more of them may be bonded to each other to form a ring or rings, comprising the step of reacting

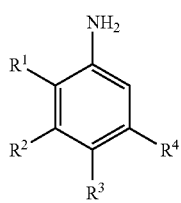

where $R^1$, $R^2$, $R^3$ and $R^4$ are defined as above, and

where Ar is defined as above, in the presence of a catalytically effective amount of $CF_3SO_3H$, or other strong acid excluding HCl or $HBF_4$, at a temperature ranging from 20 to 250° C., e.g. 100 to 200° C., with the mole ratio of (III):(IIa) ranging from 10:1 to 0.1:1, e.g., 10:1 to 2:1.

Another embodiment herein, denoted the second embodiment is directed to a method of synthesizing an aniline having a structure selected from the group consisting of

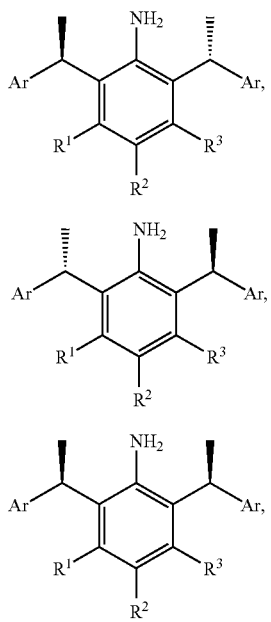

and mixtures thereof, comprising the step of reacting

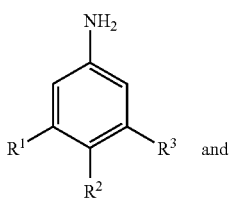

where $R^1$, $R^2$, $R^3$ and Ar are as defined in the first embodiment, in the presence of a catalytically effective amount of $CF_3SO_3H$ or other strong acid excluding HCl or $HBF_4$, at a temperature ranging from 20 to 250° C., e.g., 100 to 200° C., with the mole ratio of (III):(IIb) ranging from 10:1 to 0.1:1.

Still another embodiment herein, denoted the third embodiment is directed to a compound having the structure

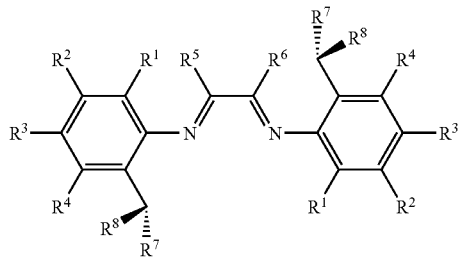

where $R^1$, $R^2$, $R^3$ and $R^4$ are as defined in the first embodiment and $R^5$ and $R^6$ may be the same or different, and are each a hydrogen atom, a halogen atom, a fluorocarbon group, a heterocyclic compound residue, an oxygen-containing group, a nitrogen-containing group, a boron-containing group, a sulfur-containing group, a phosphorus-containing group, or a silicon-containing group, and they may be bonded to each other or to one or more of $R^1$, $R^2$, $R^3$, $R^4$, $R^7$ or $R^8$ to form a ring or rings, and $R^7$ and $R^8$ are different and neither a hydrogen, and instead are each a halogen atom, a fluorocarbon group, a heterocyclic compound residue, an aromatic group, an oxygen-containing group, a nitrogen-containing group, a boron-containing group, a sulfur-containing group, a phosphorus-containing group, or a carbon-containing group (such as a hydrocarbon), silicon-containing group, and they may be bonded to each other to form a ring or rings.

In a subset of the third embodiment, the case is excluded where $R^1$ is sec-phenethyl, $R^3$ is Me, $R^5/R^6$ are H, Me, or are derived from acenaphthenequinone, $R^7$=Me, $R^8$=Ph, and all the stereogenic centers of the sec-phenethyl groups are of the same absolute configuration.

The compound of the first, second and third embodiments are useful for the preparation of the complexes of the fourth, fifth, sixth or seventh embodiments.

Still another embodiment herein, denoted the fourth embodiment is directed to a complex having the formula

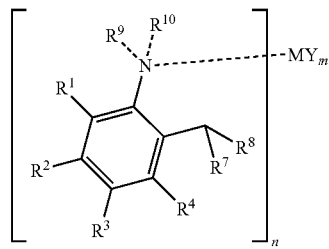

where $R^1$, $R^2$, $R^3$ and $R^4$ are defined as in the first embodiment; $R^7$, $R^8$ are defined as in the third embodiment; n is an integer from 1-3; m is an integer from 0-5; M is a group 3-11 transition metal; $R^9$ and $R^{10}$ are optional and may be the same or different, and are each a hydrogen atom, a halogen atom, a fluorocarbon group, a heterocyclic compound residue, an oxygen-containing group, a nitrogen-containing group, a boron-containing group, a sulfur-containing group, a phosphorus-containing group, or a silicon-containing group, and two or more of them may be bonded to each other to form a ring or rings; Y is a hydrogen atom, a halogen atom, an oxygen-containing group, a sulfur-containing group, a nitrogen-containing group, a boron-containing group, an aluminum-containing group, a phosphorus-containing group, a halogen-containing group, a heterocyclic compound residue, a carbon-containing group, e.g., containing from 1 to 20 carbon atoms, a silicon-containing group, a germanium-containing group or a tin-containing group, and when m is 2, 3 or 4, plural groups Y may be the same or different and may be bonded to each other or to one or more of $R^1$, $R^2$, $R^3$, $R^4$, $R^7$, $R^8$, $R^9$ or $R^{10}$ to form a ring; and the bonds between M and N are coordinative, covalent, or ionic.

Still another embodiment herein, denoted the fifth embodiment, is directed to a complex having the formula

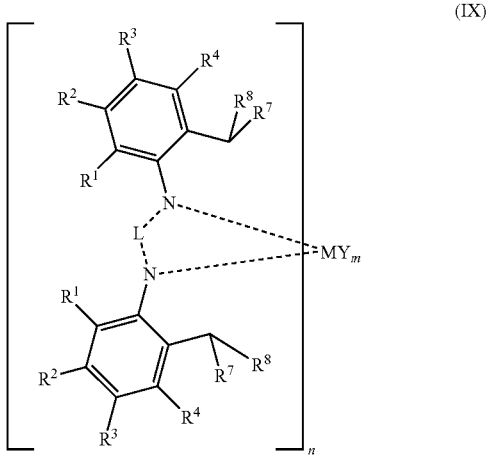

(IX)

where $R^1$, $R^2$, $R^3$, and $R^4$ are defined as in the first embodiment; $R^7$, $R^8$ are defined as in the third embodiment; n is an integer from 1-3; m is an integer from 0-4; M is a group 3-11 transition metal; L is a linking bridge that may be a carbon-containing group (such as a hydrocarbon), a silicon-containing group, or a boron-containing group; Y is a hydrogen atom, a halogen atom, an oxygen-containing group, a sulfur-containing group, a nitrogen-containing group, a boron-containing group, an aluminum-containing group, a phosphorus-containing group, a halogen-containing group, a heterocyclic compound residue, a carbon-containing group, e.g., containing from 1 to 20 carbon atoms, a silicon-containing group, a germanium-containing group or a tin-containing group, and when m is 2, 3 or 4, plural groups Y may be the same or different and may be bonded to each other to form a ring; and the bonds between M and N and L and N are coordinative, covalent, or ionic.

In a subset of the fifth embodiment, the case is excluded where $R^1$ is sec-phenethyl, $R^3$ is Me, $R^7$=Me, $R^8$=Ph, L is derived from an α-diketone, M is Ni, n is 1, $Y_m$ is $Br_2$ and all of the stereogenic centers of the sec-phenethyl groups are of the same absolute configuration.

Still another embodiment herein, denoted the sixth embodiment is directed to a complex having the formula

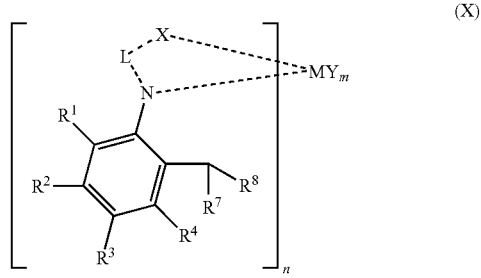

(X)

where $R^1$, $R^2$, $R^3$ and $R^4$ are defined as in the first embodiment; $R^7$, $R^8$ are defined as in the third embodiment; n is an integer from 1-3; m is an integer from 0-4; M is a group 3-11 transition metal; X is a group capable of binding to the metal, e.g. O, $OR^{11}$, $NR^{11}$, $N(R^{11})_2$, $P(R^{11})_2$, $2-C_5H_4N$, $C_5(R^{11})_4$, $R^{11}$ is optional and if plural $R^{11}$ groups are present they may be the same or different, and $R^{11}$ can be a hydrogen atom, a halogen atom, a fluorocarbon group, a heterocyclic compound residue, an oxygen-containing group, a nitrogen-containing group, a boron-containing group, a sulfur-containing group, a phosphorus-containing group, a carbon-containing group (such as a hydrocarbon), or a silicon-containing group, and two or more of them may be bonded to each other to form a ring or rings); L is a linking bridge that may be a carbon-containing group (such as a hydrocarbon), a silicon-containing group, or a boron-containing group; Y is a hydrogen atom, a halogen atom, an oxygen-containing group, a sulfur-containing group, a nitrogen-containing group, a boron-containing group, an aluminum-containing group, a phosphorus-containing group, a halogen-containing group, a heterocyclic compound residue, a carbon-containing group containing from 1 to 20 carbon atoms, a silicon-containing group, a germanium-containing group or a tin-containing group, and when m is 2, 3 or 4, plural groups Y may be the same or different and may be bonded to each other to form a ring; and the bonds between N-L, L-X, X-M, and M-N are coordinative, covalent, or ionic.

In a subset of the sixth embodiment, the case is excluded where $R^1$ is sec-phenethyl, $R^3$ is Me, $R^7$=Me, $R^8$=Ph, X=N (2,6-di-sec-phenethyl-4-methyl-phenyl), L is derived from an α-diketone, M is Ni, n is 1, $Y_m$ is $Br_2$, and all of the stereogenic centers of the sec-phenethyl groups are of the same absolute configuration.

Still another embodiment herein, denoted the seventh embodiment, is directed to a complex having the formula

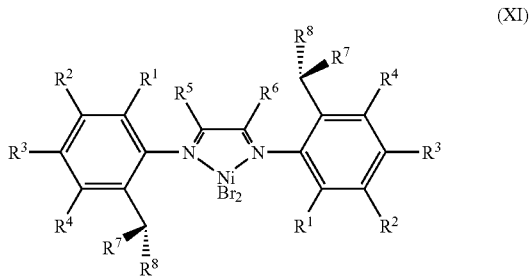

(XI)

where $R^1$, $R^2$, $R^3$ and $R^4$ are as defined in the first embodiment, and $R^5$, $R^6$, $R^7$ and $R^8$ are defined in the third embodiment.

In a subset of the seventh embodiment, the case is excluded where $R^1$ is sec-phenethyl, $R^3$ is Me, $R^5/R^6$ are derived from an alpha-diketone, and $R^7$=Me, $R^8$=Ph, and all of the stereogenic centers of the sec-phenethyl groups are of the same absolute configuration.

The complexes of the fourth, fifth, sixth and seventh embodiments are useful as catalysts for the eighth, ninth, tenth, eleventh, twelfth, thirteenth, fourteenth, fifteenth and sixteenth embodiments.

Still another embodiment herein, denoted the eighth embodiment, is directed to a method for preparing isotactic polypropylene with $T_m$ of greater than 50° C. and PDI less than 3., e.g. less than 1.5, comprising the step of polymerizing propylene in the presence of a catalytically effective amount of a complex of the fourth, fifth, sixth or seventh embodiments at a temperature ranging from −80 to 200° C., e.g. −80 to −70° C. The isotactic polypropylene is useful for food and other packaging, building materials, automotive parts, and other consumer products.

Still another embodiment herein denoted the ninth embodiment, is directed to a method for preparing regiorandom polypropylene having a percentage of 3,1-insertion of at least 1%, e.g. at least 6% or at least 20%, and PDI less than 3, e.g. less than 1.2, comprising the step of polymerizing propylene in the presence of a catalytically effective amount of the complex of any one of the fourth, fifth, sixth or seventh embodiments at a temperature ranging from −80 to 200° C., e.g. −60 to 50° C. The regiorandom polypropylene is useful as an adhesive component in an adhesive composition and as an asphalt filler material.

Still another embodiment, herein denoted the tenth embodiment, is directed to a method for preparing a block copolymer comprising a block of isotactic polypropylene of with $T_m$ of greater than 50° C. and PDI less than 3, e.g. less than 1.5, and a block of regiorandom polypropylene having a percentage of 3,1-insertion of at least 1%, e.g. at least 6% or at least 20%, and a PDI less than 3, e.g. less than 1.2, comprising polymerizing each block in the presence of a catalytically effective amount of complex of any one of the fourth, fifth, sixth, or seventh embodiments at a temperature ranging from −80 to 200° C., e.g. −80 to −70° C. followed or preceded by a temperature ranging from −80 to 200° C., e.g. −80 to 50° C. The block copolymer is useful as a compatibilizer for isotactic polypropylene and ethylene co-propylene polymers which combination is useful for making plastic wrap, films, and containers for food and other objects.

Still another embodiment herein, denoted the eleventh embodiment, is directed to regiorandom propylene based polymer, e.g., regiorandom polypropylene, having a percentage of 3,1-insertion of polypropylene ranging from 1 to 99% and a PDI of less than 2.0, e.g., less than 1.5, e.g., less than 1.2. The regiorandom propylene based polymer of the eleventh embodiment is useful as an adhesive component in an adhesive composition and as an asphalt filler material.

Still another embodiment herein, denoted the twelfth embodiment, is directed to diblock copolymer having PDI less than 3 and Mn ranging from 1,000 to 1,000,000 where one block is isotactic propylene based polymer, e.g., isotactic polypropylene, having $T_m$ of greater than 50° C. and $M_n$ ranging from 1,000 to 999,000 and one block is regiorandom propylene based polymer, e.g., regiorandom polypropylene, having a percentage of 3,1-insertion of polypropylene ranging from 1-99%, e.g. at least 6% or at least 20%, and $M_n$ ranging 1,000 to 999,000. The diblock copolymer of the twelfth embodiment is useful as a compatibilizer for isotactic polypropylene and ethylene-co-propylene polymers which combination in turn is useful for making plastic wrap, films, and containers for food and other objects.

Still another embodiment herein, denoted the thirteenth embodiment, is directed to a triblock copolymer having PDI less than 3 and $M_n$ ranging from 1,000 to 1,000,000 where a first block is isotactic propylene based polymer, e.g., isotactic polypropylene, having $T_m$ of greater than 50° C. and $M_n$ ranging from 1,000 to 998,000 and a second block is regiorandom propylene based polymer, e.g., polypropylene, having a percentage of 3,1-insertion of polypropylene ranging from 1-99%, e.g. at least 6% or at least 20%, and $M_n$ ranging 1,000 to 998,000 and a third block is isotactic propylene based polymer, e.g., isotactic polypropylene, having $T_m$ of greater than 50° C. and a $M_n$ ranging 1,000 to 998,000. The triblock copolymer of the thirteenth embodiment is useful for medical devices, such as dilation balloon catheters, e.g., as described in European 1508349 A1, shoe soles and as an adhesive component of an adhesive composition.

Still another embodiment herein, denoted the fourteenth embodiment, is directed to a multi-block copolymer having PDI less than 3 and $M_n$ ranging from 1,000 to 1,000,000 comprising at least one block of isotactic propylene based polymer, e.g., isotactic polypropylene, having $T_m$ of greater than 50° C. and $M_n$ ranging from 1,000 to 999,000 and at least one block of regiorandom propylene based polymer, e.g., regiorandom polypropylene, having a percentage of 3,1-insertion of polypropylene ranging from 1-99%, e.g. at least 6% or at least 20%, and $M_n$ ranging 1,000 to 999,000. The plural block copolymer of the plural block copolymer of the fourteenth embodiment is useful for medical devices such as dilation balloon catheters, e.g., as described in European 1508349 A1, shoe soles, and as an adhesive component in an adhesive composition.

Still another embodiment herein, denoted the fifteenth embodiment, is directed to a multi-block copolymer having PDI less than 3 and $M_n$ ranging from 1,000 to 1,000,000 comprising at least one block of ethylene based polymer, e.g. polyethylene with 1 to 100 methyl groups per 1000 methylene groups, $M_n$ ranging from 1,000 to 999,000 and at least one block of regiorandom propylene based polymer, e.g., regiorandom polypropylene, having a percentage of 3,1-insertion of polypropylene ranging from 1-99%, e.g., at least 6% or at least 20%, and $M_n$ ranging 1,000 to 999,000. The copolymer of the fifteenth embodiment is useful as a compatibilizer for polyethylene and ethylene-co-propylene and the compatibilized combination is useful for making shoe soles and as an adhesive material. The copolymer of the fifteenth embodiment is also useful for medical devices such as dilation balloon catheters, shoe soles and as an adhesive component in an adhesive composition.

Still another embodiment, herein denoted the sixteenth embodiment, is directed to a multi-block copolymer having PDI less than 3 and $M_n$ ranging from 1,000 to 1,000,000 comprising at least one block of ethylene based polymer, e.g., polyethylene, with 1 to 100 methyl groups per 1000 methylene groups, $M_n$ ranging from 1,000 to 999,000 and at least one block of poly(ethylene-co-$C_3$-$C_{10}$ alpha olefin), e.g., poly(ethylene-co-propylene) having a percentage of ethylene ranging from 1-99% and a $M_n$ ranging 1,000 to 999,000. The copolymer of the sixteenth embodiment is useful for as a compatibilizer for isotactic polypropylene and ethylene-co-propylene which compatibilizer combination is useful for medical devices, e.g., dilation balloon catheters, e.g., as described in EP 1508349 A1, shoe soles, and as an adhesive component in an adhesive composition.

Still another embodiment, herein denoted the seventeenth embodiment, is directed to a multi-block polyethylene having PDI less than 3 and $M_n$ ranging from 1,000 to 1,000,000 comprising at least one block of ethylene based polymer with 0 to 50 methyl branches per 1000 carbon atoms and $M_n$ ranging from 1,000 to 999,000 and at least one block of ethylene base polymer with more than 51 to 300 methyl branches per 1000 carbon atoms and $M_n$ ranging 1,000 to 999,000.

Yet another embodiment herein, denoted the eighteenth embodiment, is directed to a multi-block polymer made from a single monomer with branches no larger than methyl where blocks are distinguished from adjacent blocks by the chemical connectivity (also known as constitutional isomerism) of the monomer in the block. A polymer made from a single monomer also includes those polymers with a trace, e.g., less than 10% by weight, of another monomer.

Yet another embodiment herein, denoted the nineteenth embodiment, is directed to a multi-block polymer made from ethylene with branches no larger than methyl where blocks are distinguished from adjacent blocks by the chemical connectivity (also known as constitutional isomerism) of the ethylene units in the block.

Yet another embodiment, herein denoted the twentieth embodiment, is directed to a multi-block polymer made from propylene with branches no larger than methyl where blocks are distinguished from adjacent blocks by the chemical connectivity (also known as constitutional isomerism) of the propylene units in the block.

Still another embodiment, herein denoted the twenty-first embodiment, is directed to process of making a multi-block polymer from a single monomer, where blocks are distinguished from adjacent blocks by the chemical connectivity (also known as constitutional isomerism) of the monomer in the block, by changing the reaction conditions during the polymerization to result in the blocks.

Still another embodiment, herein denoted the twenty-second embodiment, is directed to process of making a multi-block polymer from a single monomer, where blocks are distinguished from adjacent blocks by the chemical connectivity of the monomer in the block, by using two or more catalysts that produce different polymer regiochemistries and can exchange polymer chains during the polymerization to result in the blocks.

Still another embodiment, herein denoted the twenty-third embodiment, is directed to a multi-block thermoplastic elastomer that does not exhibit microphase separation.

As used herein the term "regiorandom propylene based polymer" means polymer containing substantially propylene units, e.g., at least 90% propylene units, with the amount of other units present being such that the polymer remains amorphous, i.e., so as not to eliminate the amorphous nature of the material. Other units that can be present include, for example, consecutive methylene groups.

As used herein the term "isotactic propylene based polymer" means polymer containing substantially propylene units, e.g., at least 90% propylene units, with the amount of comonomer present being such as not to eliminate the crystallinity of the material. Other units that can be present include, for example, units from monomers selected from the group consisting of ethylene, $C_4$-$C_{20}$-alpha olefins, and $C_4$-$C_{20}$ alpha olefins containing functional groups, e.g., undecenyl alcohol, and combinations of these. The term "isotactic polypropylene" is used herein to mean isotactic propylene based polymer unless the context indicates otherwise.

As used herein the term "ethylene based polymer" means polymer containing substantially ethylene units, e.g., at least 90% ethylene units, with an amount of comonomer present that does not eliminate the crystallinity of the material. Other units that may be present include, for example, units from monomers selected from the group consisting of propylene, $C_4$-$C_{20}$ alpha olefins, containing functional groups such as $C_4$-$C_{20}$ alpha olefins and combinations of these.

As used herein the term "multi-block" means more than one block and is synonymous with the term "plural block".

DETAILED DESCRIPTION

The other strong acids for the first and second embodiments can be, for example, H—Y zeolite (e.g., Linde LZ-Y82), HBr, $CF_3CO_2H$, HNO3, $H_2SO_4$ or p-toluene sulfonic acid.

Turning now to M for the fourth, fifth and sixth embodiments, very good results have been obtained when M in (VIII), (IX) or (X) is Ni. Besides Ni, the best metals for metallizing (VII) are considered to be Pd and Co. Besides Ni, M in (VIII), and (IX) can be, for example, Pd, Co, Ti, Zr, Hf, Cr, Rh, Ir, Fe, Ru, Cu, Ag or Zn. An element of novelty in the fifteenth and sixteenth embodiments is the branching in the PE block as indicated by the clause "1-100 methyl groups per 1000 methylene groups."

Elements of the invention and working examples are found in Cherian, A. E. et al, "A $C_2$-Symmetric, Living, α-diimine Ni(II) catalyst regioblock copolymers from propylene," J. Am. Chem. Soc., 127(40), 13770-13771 (October 2005, referred to hereinafter as "Cherian (I) and supporting information therefore, and in Cherian, A. E. et al, "Acid-catalyzed ortho alkylation of anilines with styrenes: an improved route to chiral anilines with bulky substituents," Org. Lett. 7(23), 5135-7 (Nov. 10, 2005, referred to hereinafter as Cherian (II), and supporting information therefore. The whole of Cherian (I) and the supporting information therefore and the whole of Cherian II and the supporting information therefore are incorporated herein by reference.

Products 2, 5, 6, 7, 8, 9, 10 and 11 of Table I at page 5136 of Cherian (II) are embraced by the first embodiment herein. They are made as described in the footnotes to said Table I and as set forth at pages S2, S3, S4, S5, S6, and S7 of the supporting information for Cherian (II).

Products 3, 13, 14 and 15 of Table II at page 5137 of Cherian (II) are embraced by the second embodiment herein. They are made as described in the footnotes to Table II and at pages S2, S7, S8, and S9 of the supporting information for Cherian (II).

The ligand of complex rac 1 of page 13770 of Cherian (I) is embraced by the third embodiment herein. This ligand is made by first making product 15 of Cherian (II), the making of which is described at pages S8 and S9 of supporting information for Cherian (II). The making of this product is also described at page S3 of supporting information for Cherian (I) where it is referred to as rac-4-methyl-2-(sec-(2,4,6-trimethylphenethyl) aniline referred to hereinafter as "MTMPEA." MTMPEA is reacted with acenaphthene to form said ligand. This reaction is described at pages S3 and S4 of supporting information for Cherian (I) where the ligand is described as rac-ArN=C(An)C=NAr where Ar is 4-methyl-2-(sec-2,4,6-trimethylphenethyl) phenyl and An is acenaphthene.

Complex rac-1 is made from said ligand as described at page S4 of supporting information for Cherian (I). The complex rac-1 is embraced by the fourth, fifth, sixth and seventh embodiments herein. Other complexes embraced by the fourth, fifth, sixth, and seventh embodiments herein are prepared by reacting aniline of the first and second embodiments herein with acenaphthene and metallizing the formed intermediate by reacting it with (DME) MBr$_2$ (DME=1,2-dimethoxyethane, e.g., (DME) NiBr$_2$).

A general procedure for polymerization of propylene using the complex rac-1 or corresponding complex of other anilines of the first and second embodiments is described at page S4 of supporting information for Cherian (I).

Examples of compounds meeting the seventh embodiment and their making are indicated in the table below.

herein, followed by the removal of ethylene and addition of propylene and polymerization at 0° C., and finally removal of the propylene and re-addition of ethylene and polymerization at 0° C.

Polymers of the sixteenth embodiment herein can be made by polymerizing ethylene at 0° C. in the presence of complexes of the fourth, fifth, sixth or seventh embodiments herein, followed by the addition of propylene to the ethylene

TABLE (XI)

| Entry[a] | R[1] | R[2] | R[3] | R[4] | R[5]/R[6] | R[7] | R[8] | Yield (mg) | TOF[b] (h$^{-1}$) | % 3,1-insertions[c] | M$_n$[d] (g/mol) | M$_w$/M$_n$[d] | T$_g$[e] (° C.) | T$_m$[e] (° C.) |
|---|---|---|---|---|---|---|---|---|---|---|---|---|---|---|
| 1 | F | H | CH$_3$ | H | acenaphthyl | CH$_3$ | 2,4,6-Me$_3$Ph | 120 | 6 | 7.6 | 9,200 | 1.34 | n.d.[f] | 135.6 |
| 2 | H | H | CH$_3$ | H | acenaphthyl | CH$_3$ | 2,4,6-Me$_3$Ph | 90 | 4 | — | 3,700 | 2.05 | — | — |
| 3[g] | H | CH$_3$ | H | H | acenaphthyl | CH$_3$ | 2,4,6-Me$_3$Ph | 280 | 14 | 13.7 | 18,000 | 1.26 | — | — |
| 4[g] | CH$_3$ | H | CH$_3$ | H | acenaphthyl | CH$_3$ | 4-$^t$BuPh | 3030 | 212 | 14.5 | 101,600 | 1.09 | −19.9 | n.d.[f] |

[a]Polymerization conditions: toluene = 25 mL, Ni = 17 micromol, [Al]/[Ni] = 260, propylene = 15 g, T$_{rxn}$ −60° C., 24 hours.
[b]TOF (turnover frequency) is the number of moles propylene reacted per mole Ni per hour.
[c]Determined by $^1$H NMR using the equation: % 3,1-insertions = [(1000 − B)/(1000 + 2B)] * 100%, where B = CH$_3$/1000 CH$_2$.
[d]Determined by gel permeation chromatography (vs. polystyrene standards).
[e]Determined by differential scanning calorimetry (second heat).
[f]None detected.
[g]Propylene = 5 g, T$_{rxn}$ −40° C.

The polymerization in Table 1, entry 6, of Cherian (I) is embraced by the eighth embodiment herein.

The polymerization in Table 1, entries 1-5 of Cherian (I) are embraced by the ninth embodiment herein.

A general procedure for diblock polymerization wherein one block is isotactic polypropylene and the second block is regiorandom polypropylene is described at page S5 of the supporting information for Cherian (II) except that the first polymerization is carried out at −78° C. instead of −60° C. Other complexes as described above can be substituted for complex rac-1. These polymerizations meet the tenth embodiment herein.

Polymerizations described at page 13771 of Cherian (I), second to the last paragraph of the text of Cherian (I) are embraced by the tenth embodiment herein.

The polymers formed in the polymerizations of Table 1, entries 1-5, at page 13771 of Cherian (I), are embraced by the eleventh embodiment herein.

Polymers described in the text at page 13771 of Cherian (I), second to the last paragraph, are embraced by the twelfth, thirteenth and fourteenth embodiments herein.

Polymers of the fifteenth embodiment herein can be made by polymerizing ethylene at 0° C. in the presence of complexes of the fourth, fifth, sixth or seventh embodiments and polymerization at 0° C., and finally removal of the propylene/ethylene mix and re-addition of ethylene and polymerization at 0° C.

The multi-block polymer of the seventeenth embodiment is illustrated by [(CH$_2$)$_n$-block-((CH$_2$)$_x$—(CHMe)$_{1-x}$)$_m$]$_o$ and can be made by polymerizing ethylene with a catalyst, such as one based on complex XI, and changing the temperature of the polymerization to change the branching ratio.

The multi-block polymer of the eighteenth embodiment is illustrated by [(CH$_2$)$_n$-block-((CH$_2$)$_x$—(CHMe)$_{1-x}$)$_m$]$_o$ and can be made by polymerizing 1-hexene with a catalyst, such as one based on complex XI, and changing the temperature of the polymerization to change the branching ratio.

The multi-block polymer of the nineteenth embodiment is illustrated by [(CH$_2$)$_n$-block-((CH$_2$)$_x$—(CHMe)$_{1-x}$)$_m$]$_o$ and can be made by polymerizing ethylene with a catalyst, such as one based on complex XI, and changing the temperature of the polymerization to change the branching ratio.

The multi-block polymer of the twentieth embodiment is illustrated by [(CH$_2$)$_n$-block-((CH$_2$)$_x$—(CHMe)$_{1-x}$)$_m$]$_o$ and can be made by polymerizing propylene with a catalyst, such as one based on complex XI, and changing the temperature of the polymerization to change the branching ratio.

In the seventeenth, eighteenth, nineteenth and twentieth embodiments, in the recited formulas, m and n each range from 20 to 10,000 and x ranges from 0.999 to 0.5 and $M_n$ ranges from 1,000 to 1,000,000 grams/mole.

The process of the twenty-first embodiment is illustrated by the following process conditions: ethylene is polymerized with a catalyst, such as one based on complex XI, and the reaction temperature is changed during the polymerization to give regions of different chemical connectivity.

The process of the twenty-second embodiment is illustrated by the following process conditions: propylene is polymerized with two living catalysts that exhibit different regioselectivities, such as one based on complex XI and another complex such as a non-metallocene group IV catalyst, and bimetallic exchange of polymer chains during the polymerization gives regions of different chemical connectivity.

The elastomer of the twenty-third embodiment is illustrated by (isotactic PP)-block-(regiorandom PP)-block-(isotactic PP) which can be made by sequentially polymerizing propylene with the catalyst based on complex XI at −60° C., then 0° C., then finally −60° C. The elastomer resists chain pull out which causes tendency to rupture, and therefore has less tendency to rupture than other thermoplastic elastomers.

The term "microphase separation" is used herein to mean separation of the blocks of the polymers into two different regimes on a 1 micron or smaller basis.

When there is no such separation present, crystallites are present (but N.B., the material is elastomeric), and the material can be of higher melting point than if microphase separation is present. Microphase separation occurs when a block copolymer has two blocks that are not miscible; these two blocks want to separate like oil and water, but they are covalently attached to each other, and can only separate on the micrometer/nanometer scale.

Variations

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. Multi-block copolymer having PDI less than 3 and $M_n$ ranging from 1,000 to 1,000,000 comprising at least one block of isotactic propylene based polymer having $T_m$ greater than 50° C. and $M_n$ ranging from 1,000 to 999,000 and at least one block of regiorandom propylene based polymer having a percentage of 3,1-inserted polypropylene units ranging from 1-99 mole percent, and a $M_n$ ranging 1,000 to 999,000.

2. Multi-block copolymer as claimed in claim 1 where the regiorandom propylene based polymer consists of regiorandom polypropylene.

3. A multi-block copolymer according to claim 1 which is a triblock copolymer where a first block is isotactic propylene based polymer having $T_m$ greater than 50° C. and $M_n$ ranging from 1,000 to 998,000 and a second block is regiorandom propylene based polymer having a percentage of 3,1-inserted of propylene units ranging from 1-99 mole %, and a $M_n$ ranging from 1,000 to 998,000, and a third block is isotactic propylene based polymer having $T_m$ greater than 50° C. and a $M_n$ ranging 1,000 to 998,000.

4. A multi-block copolymer according to claim 3 where the regiorandom propylene based polymer consists of regiorandom polypropylene.

* * * * *

UNITED STATES PATENT AND TRADEMARK OFFICE
CERTIFICATE OF CORRECTION

PATENT NO. : 7,560,523 B2  
APPLICATION NO. : 11/508333  
DATED : July 14, 2009  
INVENTOR(S) : Geoffrey W. Coates et al.

Page 1 of 1

It is certified that error appears in the above-identified patent and that said Letters Patent is hereby corrected as shown below:

Claim 3 (Column 14, line 24), delete "of".

Signed and Sealed this

Eighteenth Day of August, 2009

David J. Kappos  
*Director of the United States Patent and Trademark Office*